(12) United States Patent
Kwok

(10) Patent No.: US 9,162,035 B2
(45) Date of Patent: *Oct. 20, 2015

(54) RECOGNITION SYSTEM FOR AN APPARATUS THAT DELIVERS BREATHABLE GAS TO A PATIENT

(75) Inventor: Philip Rodney Kwok, Chatswood (AU)

(73) Assignee: RESMED LIMITED, Bella Vista, New South Wales (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/588,556

(22) Filed: Aug. 17, 2012

(65) Prior Publication Data

US 2012/0304994 A1    Dec. 6, 2012

Related U.S. Application Data

(62) Division of application No. 11/794,150, filed as application No. PCT/AU2006/000238 on Feb. 24, 2006, now Pat. No. 8,267,084.

(60) Provisional application No. 60/656,880, filed on Mar. 1, 2005.

(51) Int. Cl.
*F16K 31/02* (2006.01)
*A61M 16/08* (2006.01)
*A61M 16/00* (2006.01)

(52) U.S. Cl.
CPC ....... *A61M 16/0816* (2013.01); *A61M 16/0066* (2013.01); *A61M 16/0875* (2013.01); *A61M 2205/6018* (2013.01); *A61M 2205/6027* (2013.01); *A61M 2205/6045* (2013.01)

(58) Field of Classification Search
CPC ............... A61M 16/0166; A61M 16/0816; A61M 16/0875; A61M 2205/6018; A61M 2205/6027; A61M 2205/6045
USPC ............ 128/200.24, 202.27, 204.18–204.23, 128/204.26, 205.22, 912
See application file for complete search history.

(56) References Cited

U.S. PATENT DOCUMENTS

| 4,695,955 A | 9/1987 | Faisandier |
| 4,768,496 A | 9/1988 | Kreizman et al. |

(Continued)

FOREIGN PATENT DOCUMENTS

| DE | 40 20 522 | 1/1992 |
| EP | 1 516 641 | 3/2005 |

(Continued)

OTHER PUBLICATIONS

Examiner's First Report issued in related Australian Appln. No. 2006220222 (Nov. 8, 2010).

(Continued)

*Primary Examiner* — Tan-Uyen (Jackie) T Ho
*Assistant Examiner* — Mark K Han
(74) *Attorney, Agent, or Firm* — Nixon & Vanderhye P.C.

(57) ABSTRACT

An adapter for use with a flow generator includes a conduit attachable to the outlet of the flow generator and an identifying element supported by the conduit and providing an identifying feature unique to a specific peripheral component attachable to the flow generator. The identifying feature is communicatable to the flow generator so that appropriate operating parameters of the flow generator may be automatically selected by the flow generator to coordinate with the specific peripheral component.

19 Claims, 11 Drawing Sheets

(56) References Cited

U.S. PATENT DOCUMENTS

| | | | |
|---|---|---|---|
| 4,944,310 A | 7/1990 | Sullivan | |
| 5,413,097 A * | 5/1995 | Birenheide et al. | 128/206.17 |
| 5,647,352 A | 7/1997 | Niemi et al. | |
| 5,660,567 A | 8/1997 | Nierlich et al. | |
| 5,813,404 A | 9/1998 | Devlin et al. | |
| 5,950,621 A | 9/1999 | Klockseth | |
| 6,035,851 A | 3/2000 | Wallen | |
| 6,126,610 A | 10/2000 | Rich et al. | |
| 6,142,949 A | 11/2000 | Ubby | |
| 6,158,430 A * | 12/2000 | Pfeiffer et al. | 128/202.27 |
| 6,186,140 B1 * | 2/2001 | Hoague | 128/202.22 |
| 6,571,792 B1 | 6/2003 | Hendrickson et al. | |
| 6,910,483 B2 | 6/2005 | Daly et al. | |
| 7,140,367 B2 | 11/2006 | White et al. | |
| 7,148,806 B2 * | 12/2006 | Anttila et al. | 340/573.1 |
| RE40,365 E | 6/2008 | Kirchgeorg et al. | |
| 7,424,889 B2 * | 9/2008 | Mashak | 128/205.28 |
| 7,469,698 B1 | 12/2008 | Childers et al. | |
| 7,527,053 B2 | 5/2009 | DeVries et al. | |
| 7,607,437 B2 | 10/2009 | Boyle et al. | |
| 7,891,353 B2 * | 2/2011 | Chalvignac | 128/204.21 |
| 7,913,689 B2 | 3/2011 | Henry et al. | |
| 7,987,847 B2 * | 8/2011 | Wickham et al. | 128/204.21 |
| 7,997,885 B2 | 8/2011 | Allum | |
| 8,006,691 B2 | 8/2011 | Kenyon et al. | |
| 8,210,173 B2 * | 7/2012 | Vandine | 128/204.21 |
| 8,210,178 B2 * | 7/2012 | Schermeier et al. | 128/205.28 |
| 8,267,084 B2 * | 9/2012 | Kwok | 128/204.21 |
| 8,381,725 B2 * | 2/2013 | Chalvignac | 128/204.21 |
| 8,496,001 B2 | 7/2013 | Schermeier et al. | |
| 2001/0017134 A1 | 8/2001 | Bahr | |
| 2002/0144682 A1 | 10/2002 | Kurger et al. | |
| 2002/0174867 A1 | 11/2002 | Gunaratnam et al. | |
| 2003/0154977 A1 | 8/2003 | White et al. | |
| 2003/0154981 A1 | 8/2003 | Spruiell | |
| 2003/0196662 A1 | 10/2003 | Ging et al. | |
| 2004/0074495 A1 | 4/2004 | Wickham et al. | |
| 2004/0163647 A1 | 8/2004 | Figley et al. | |
| 2004/0171982 A1 | 9/2004 | Danchin | |
| 2004/0182386 A1 | 9/2004 | Meier | |
| 2004/0210151 A1 | 10/2004 | Tsukashima et al. | |
| 2004/0226566 A1 | 11/2004 | Gunaratnam et al. | |
| 2005/0061318 A1 * | 3/2005 | Faram | 128/204.18 |
| 2005/0211761 A1 * | 9/2005 | Anttila et al. | 235/376 |
| 2006/0231092 A1 * | 10/2006 | Mashak | 128/200.23 |
| 2006/0278220 A1 * | 12/2006 | Schermeier et al. | 128/203.12 |
| 2007/0000491 A1 * | 1/2007 | Chalvignac | 128/204.23 |
| 2007/0144519 A1 | 6/2007 | Henry | |
| 2008/0078387 A1 * | 4/2008 | Vandine | 128/204.21 |
| 2010/0147301 A1 | 6/2010 | Kwok | |
| 2010/0236552 A1 | 9/2010 | Kwok et al. | |
| 2011/0139153 A1 * | 6/2011 | Chalvignac | 128/204.21 |
| 2011/0139154 A1 | 6/2011 | Henry et al. | |
| 2012/0318266 A1 * | 12/2012 | Chou | 128/204.23 |

FOREIGN PATENT DOCUMENTS

| | | |
|---|---|---|
| EP | 1 579 884 | 9/2005 |
| JP | H04-158856 | 6/1992 |
| JP | 2002-172170 | 6/2002 |
| JP | 2003-061977 | 3/2003 |
| JP | 2004-532666 | 10/2004 |
| WO | 02/053217 | 7/2002 |
| WO | 2004-060443 | 7/2004 |
| WO | 2004-112873 | 12/2004 |
| WO | 2005/002655 | 1/2005 |
| WO | 2005/067520 | 7/2005 |
| WO | 2006-125252 | 11/2006 |
| WO | 2007-059810 | 3/2007 |

OTHER PUBLICATIONS

Ofice Action issued in related Japanese Appln. No. 2007-557276 (May 10, 2011) w/English translation.
Office Action issued in related European Appln. No. 06704913.0 (Oct. 20, 2011).
International Search Report for PCT/AU2006/000238 mailed Apr. 26, 2006.
Supplementary Partial European Search Report for EP 06704913 mailed Oct. 20, 2011.
International Preliminary Report on Patentability for PCT/AU2006/000238 mailed Sep. 11, 2007.
Written Opinion for PCT/AU2006/000238 mailed Apr. 20, 2006.
International Search Report for PCT/AU2006/001169, mailed Nov. 29, 2006.
Office Action for European Application No. 06126895.9, mailed Oct. 29, 2012.
Office Action for U.S. Appl. No. 13/032,178, mailed Feb. 6, 2014.
Kwok, U.S. Appl. No. 60/656,880, filed Mar. 1, 2005.
Kwok, U.S. Appl. No. 60/707,950, filed Aug. 15, 2006.
Japanese Office Action issued in JP 2006-344662 issued on Nov. 22, 2011 with English Language Translation.

* cited by examiner

| Mask Type | Resistance Detected |
|---|---|
| Activa® | 1 ohm |
| Mirage® | 2 ohm |
| UltraMirage® | 3 ohm |

RECOGNITION SYSTEM FOR AN APPARATUS THAT DELIVERS BREATHABLE GAS TO A PATIENT

CROSS REFERENCE TO RELATED APPLICATION

This application is a continuation of application Ser. No. 11/794,150, now U.S. Pat. No. 8,267,084, filed Oct. 29, 2008; which is the national stage of International Application No. PCT/AU2006/000238, under 35 U.S.C. 371, filed Feb. 24, 2006; which claims the benefit of provisional Application No. 60/656,880, filed Mar. 1, 2005, the entire contents of which are hereby incorporated by reference in this application.

FIELD OF THE INVENTION

The present invention relates to an apparatus that delivers breathable gas to a patient.

BACKGROUND OF THE INVENTION

Apparatus to deliver breathable gas to a patient typically includes a flow generator, an air delivery conduit, and a patient interface. Prior to use, operating parameters of the flow generator, e.g., treatment pressure, need to be manually adjusted by the patient to coordinate with the peripheral components, e.g., patient interface, being used. For example, known flow generators include a menu system that allows the patient to select the type of peripheral components being used, e.g., by brand, method of delivery, etc. Once the components are selected by the patient, the flow generator can select appropriate operating parameters of the flow generator that best coordinate with the selected components.

The present invention provides improvements to known apparatus to facilitate the coordination between the flow generator and the peripheral components.

SUMMARY OF THE INVENTION

One aspect of the invention is directed towards a recognition system that provides structure to facilitate the coordination between the flow generator and the peripheral components.

Another aspect of the invention relates to an adapter for use with a flow generator that generates a supply of pressurized air to be provided at an outlet to a patient for treatment. The adapter includes a conduit attachable to the outlet of the flow generator, and an identifying element supported by the conduit and providing an identifying feature unique to a specific peripheral component attachable to the flow generator. The identifying feature is communicatable to the flow generator so that appropriate operating parameters of the flow generator may be automatically selected by the flow generator to coordinate with the specific peripheral component.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate, an understanding of the various embodiments of this invention. In such drawings.

DETAILED DESCRIPTION OF ILLUSTRATED EMBODIMENTS

Figure 1:
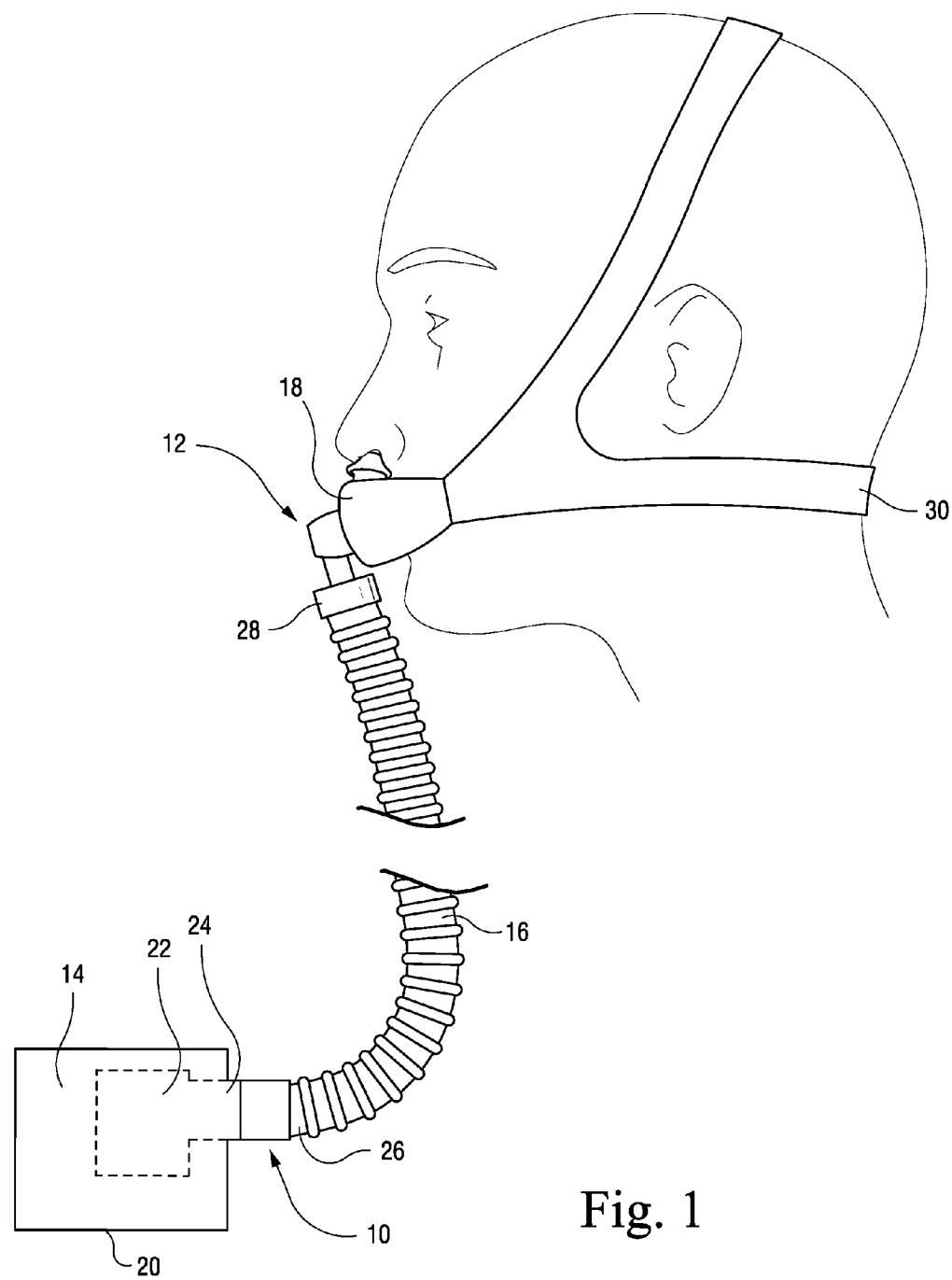
FIG. 1 is a side view of an embodiment of an apparatus that delivers breathable gas to a patient, the apparatus including a recognition system constructed according to an embodiment of the present invention.

FIGS. 1-9 illustrate a recognition system 10 constructed according to an embodiment of the present invention. The recognition system 10 is structured for use with an apparatus 12 that delivers a supply of pressurized breathable air to a patient for treatment, e.g., of Sleep Disordered Breathing (SDB) with CPAP or Non-Invasive Positive Pressure Ventilation (NIPPY). As best shown in FIG. 1, the apparatus 12 generally includes a flow generator 14, an air delivery conduit 16, and a patient interface 18. As discussed in greater detail below, the recognition system 10 allows the flow generator 14 to automatically recognize or identify one or more of the peripheral components selected by the patient so that appropriate operating parameters of the flow generator 14 may be automatically selected by the flow generator 14 to coordinate with the selected peripheral components.

The flow generator 14 is structured to generate a supply of pressurized air to be provided to a patient for treatment. The flow generator 14 includes a housing 20 and a blower 22 supported within the housing 20. As is known in the art, the blower 22 is operable to draw a supply of air into the housing 20 through one or more intake openings and provide a pressurized flow of air at an outlet 24 (see FIGS. 1, 4, and 5).

The supply of pressurized air is delivered to the patient via the air delivery conduit 16 that includes one end 26 coupled to the outlet 24 of the flow generator 14 and an opposite end 28 coupled to the patient interface 18, as shown in FIG. 1.

The patient interface 18 comfortably engages the patient's face and provides a seal. The patient interface 18 may have any suitable configuration as is known in the art, e.g., full-face mask, nasal mask, oro-nasal mask, mouth mask, nasal prongs, etc. Also, any suitable headgear arrangement 30 may be utilized to comfortably support the patient interface 18 in a desired position on the patient's face.

Figure 2:
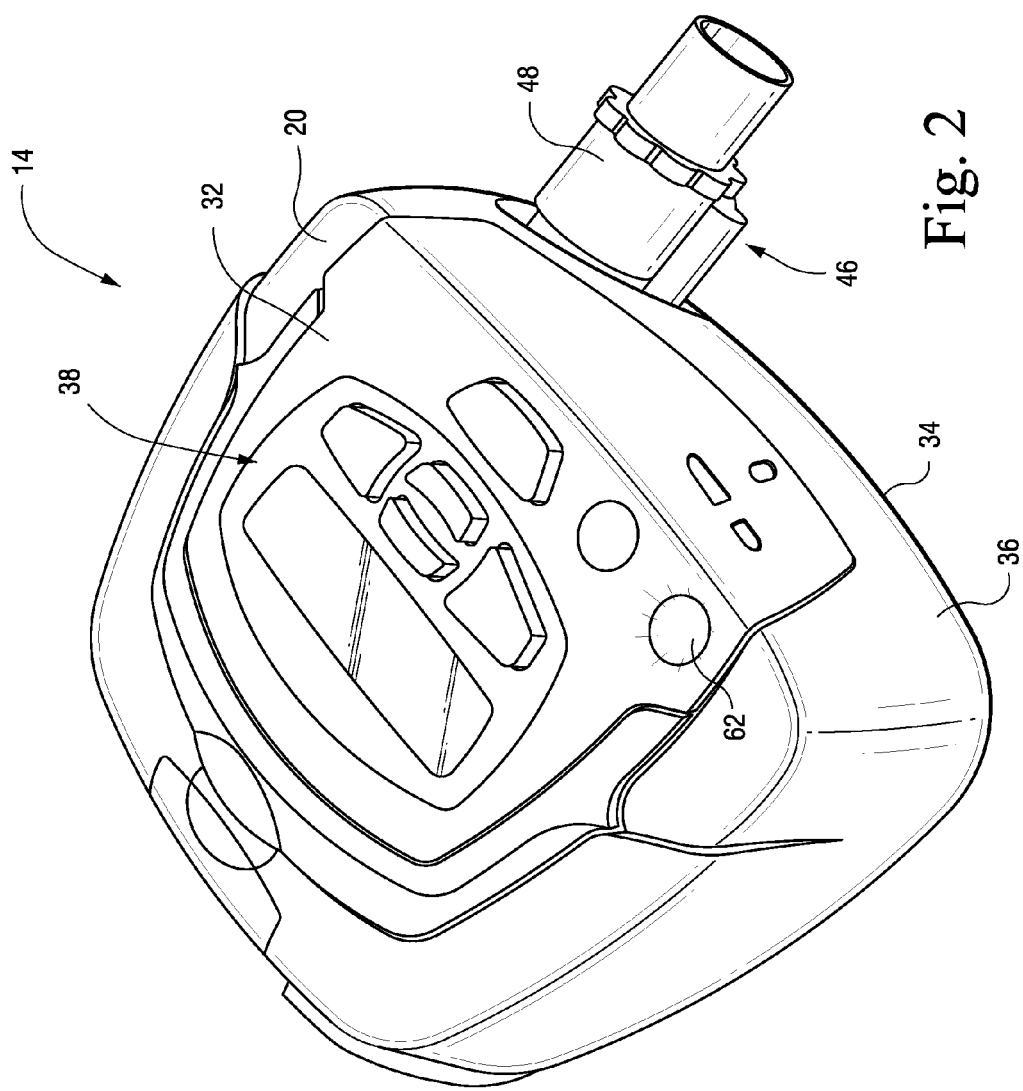
FIG. 2 is a top perspective view illustrating a flow generator incorporating the recognition system shown in FIG. 1, and one of the indicator lights being activated.
Figure 3:
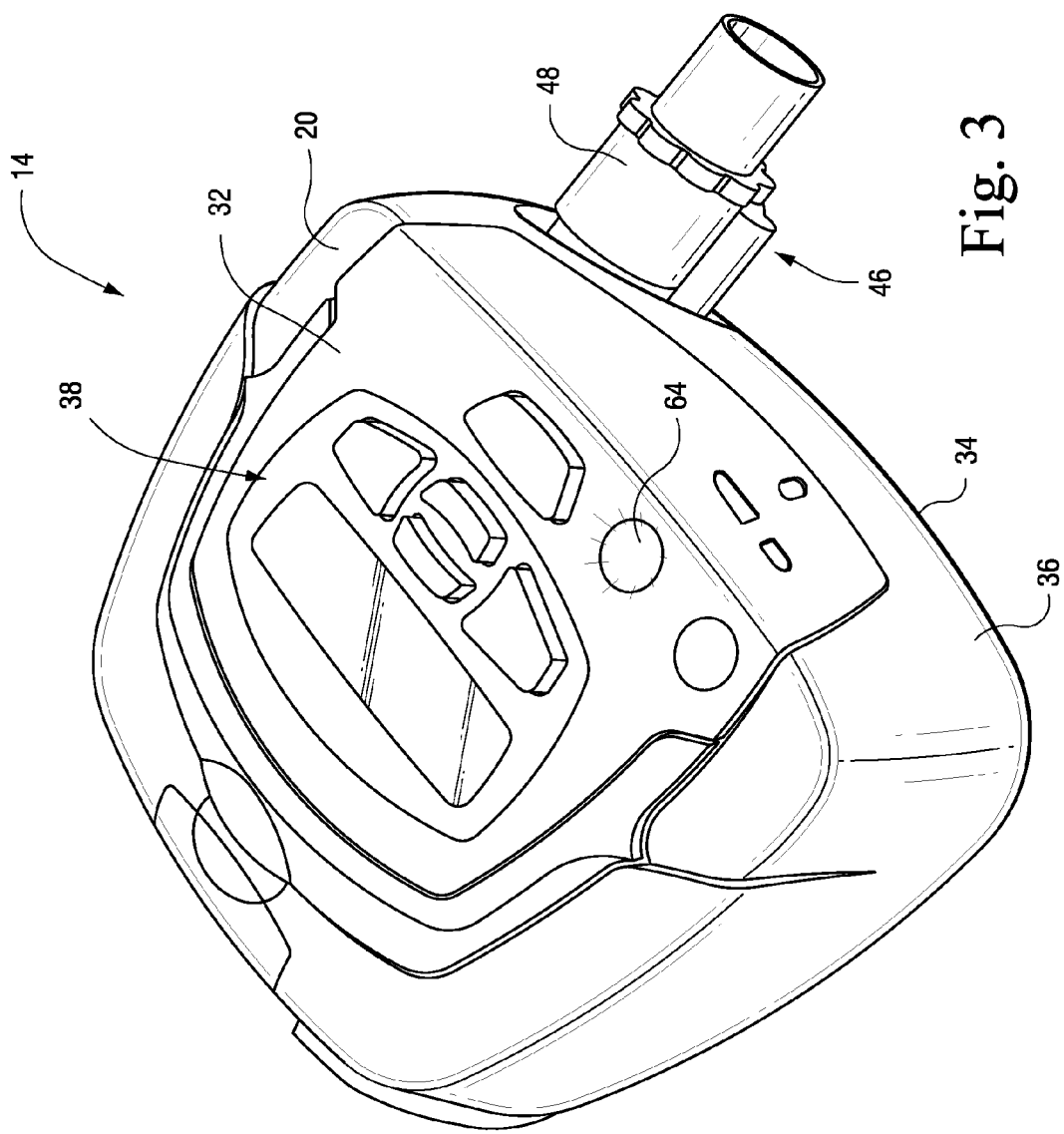
FIG. 3 is a top perspective view similar to FIG. 2 with another of the indicator lights being activated.
Figure 4:
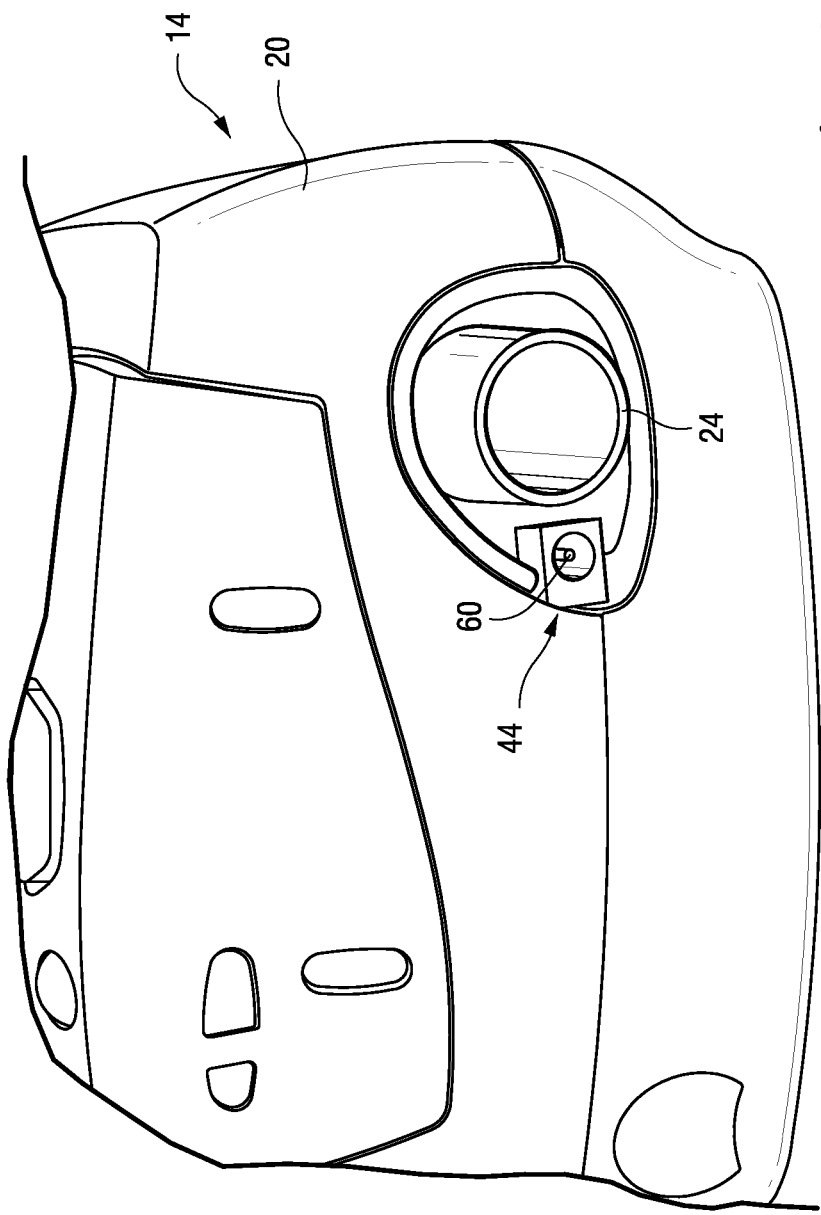
FIG. 4 is a front perspective view of the flow generator shown in FIG. 2 with an adapter of the recognition system removed.
Figure 5:
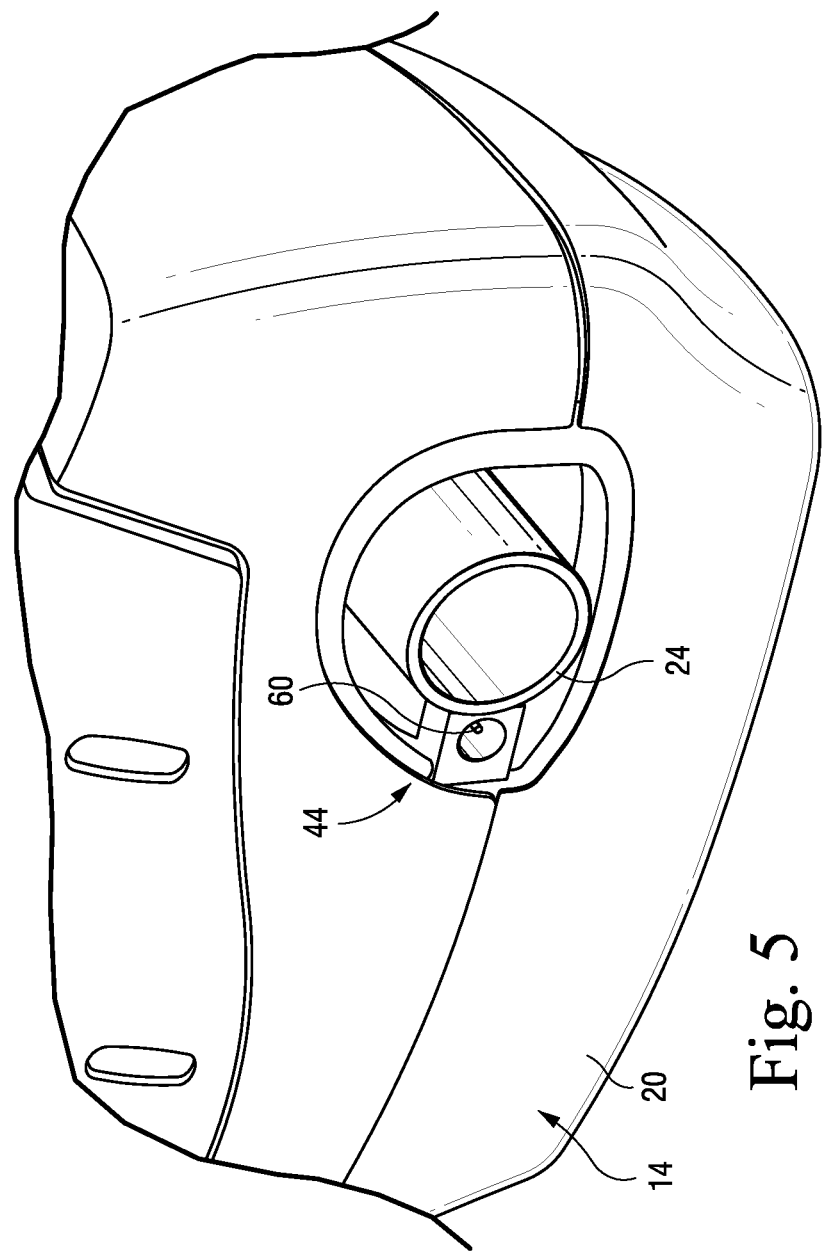
FIG. 5 is an enlarged front perspective view of the flow generator shown in FIG. 4.

As best shown in FIGS. 2-4, the housing 20 of the flow generator 14 includes an upper wall 32, a lower wall 34, and side walls 36 that interconnect the upper and lower walls 32, 34. In the illustrated embodiment, the outlet 24 is provided in one of the side walls 36. Also, the upper wall 32 incorporates a manual control unit 38 for adjusting one or more parameters of the flow generator 14, e.g., treatment pressure. However, the outlet 24 and/or control unit 38 may be incorporated into any of the walls of the housing 20. Also, it should be understood that the flow generator 14 may include additional features incorporated into the housing 20, e.g., power supply.

Figure 6:
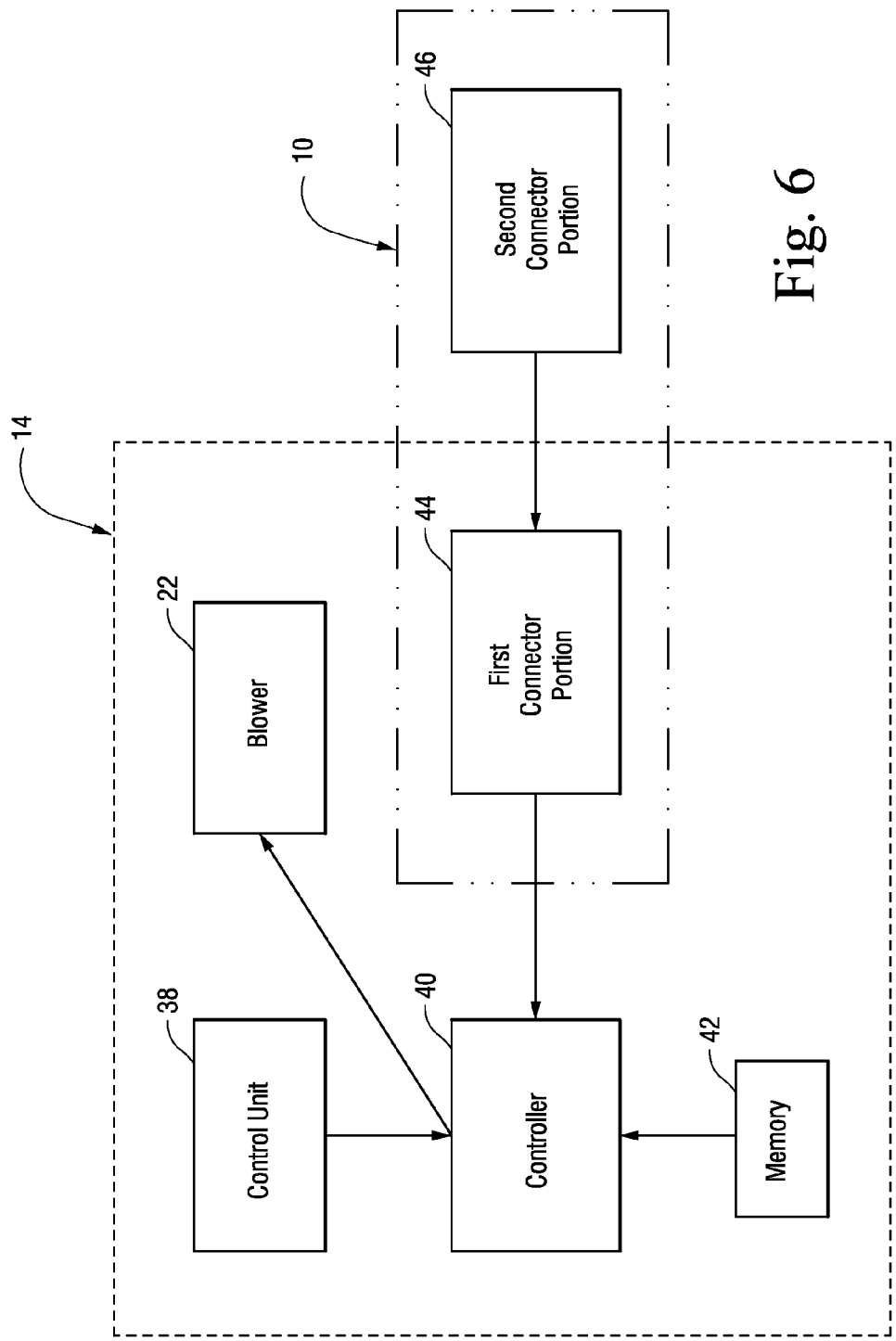
FIG. 6 is a schematic diagram of the flow generator and recognition system shown in FIG. 2.
Figure 7:
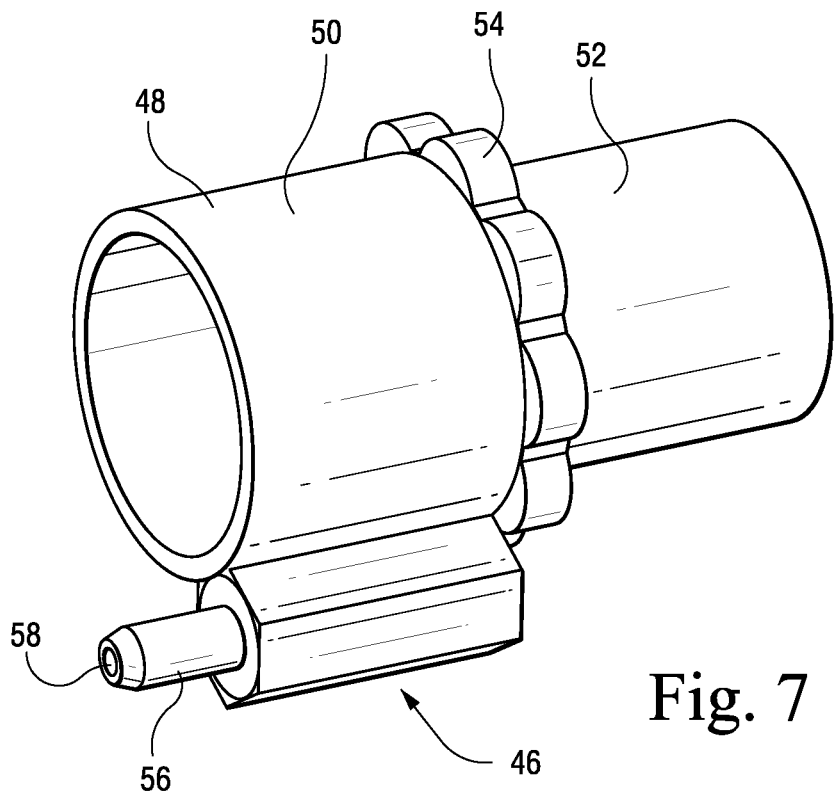
FIG. 7 is a perspective view of an adapter of the recognition system shown in FIG. 2.
Figure 8:
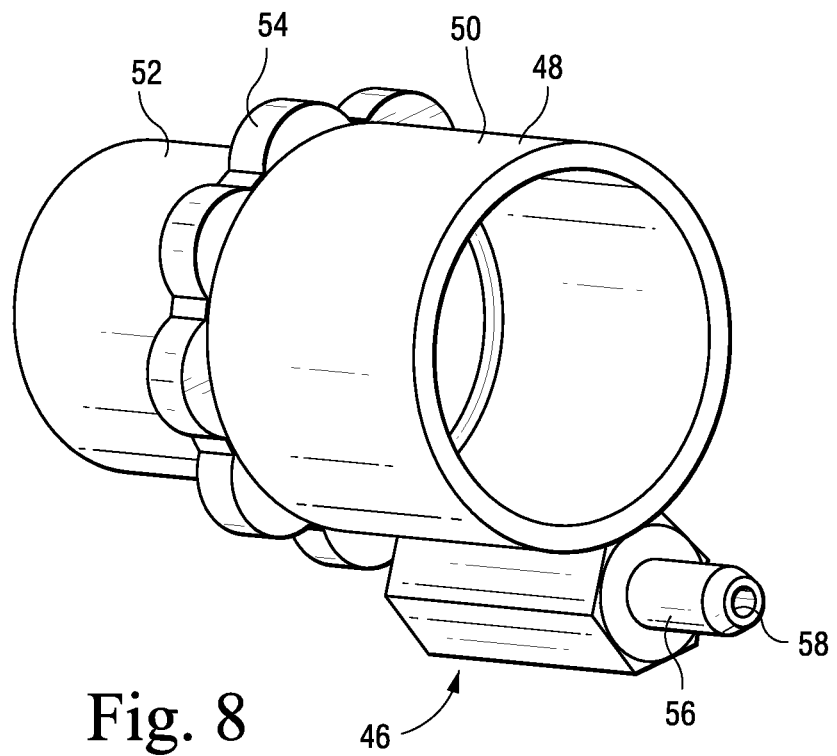
FIG. 8 is a perspective view, from a different angle, of the adapter shown in FIG. 7.

As shown in FIG. 6, the flow generator 14 includes a controller 40 operable to receive input signals and to control operation of the blower 22 based on input signals. Input signals may be provided by the control unit 38 which has a plurality of control features that can be manually selected by the patient to adjust various parameters of the flow generator 14. For example, the patient may select the type of patient interface 18 being used, e.g., via a menu system of the control unit 38, so that the controller 40 can adjust the blower outlet pressure so that it coordinates with the selected patient interface 18. The controller 40 may include a memory 42 that stores preferred operating parameters for a variety of patient interfaces, e.g., by brand or method of delivery. When the controller 40 receives the input signal regarding the selected patient interface 18 from the control unit 38, the controller 40 can operate the blower 22 based on the stored operating parameters in the memory 42 for the selected patient interface 18. Alternatively, the preferred operating parameters for a selected patient interface 18 may be entered manually through the control unit 38.

Connector Recognition

The recognition system 10 is provided to allow the controller 40 of the flow generator 14 to automatically recognize one or more peripheral components, e.g., the patient interface 18, so that the patient does not have to utilize the control unit 38. Moreover, the recognition system 10 may allow the apparatus 12 to operate more efficiently as the recognition system 10 enables the flow generator 14 to select operating parameters that are specifically optimized for the selected peripheral components.

In the illustrated embodiment, the recognition system 10 includes a first connector portion 44 provided by the flow generator 14 (e.g., see FIGS. 4, 5, and 6), and a second connector portion 46 adapted to be removably coupled with the first connector portion 44 (e.g., see FIGS. 2, 3, and 6-9). The second connector portion 46 is associated with a specific peripheral component, e.g., patient interface 18, and includes an identifying feature unique to the specific peripheral component. The first connector portion 44 includes structure to communicate the identifying feature of the second connector portion 46 to the controller 40 so that the controller 40 can recognize the identifying feature and hence the associated peripheral component. The controller 40 can then select appropriate operating parameters of the blower 22, e.g., via memory 42, to coordinate with the associated peripheral component. For example, the blower 22 may be controlled so that the blower outlet pressure is relatively lower for one group of patient interfaces, e.g., nasal, and relatively higher for another group of patient interfaces, e.g., nasal and mouth.

As shown in FIGS. 2, 3, and 7-9, the second connector portion 46 is provided on an adapter 48 that is adapted to interconnect the outlet 24 of the flow generator 14 and the end 26 of the air delivery conduit 16. Specifically, the adapter 48 is in the form of a conduit including a first end portion 50 attachable to the outlet 24 and a second end portion 52 attachable to the air delivery conduit 16. As illustrated, first end portion 50 has a greater diameter than the second end portion 52. However, the end portions 50, 52 may have any suitable arrangement, e.g., similar diameters. Also, a gripping portion 54, in the form of spaced contoured ribs, is provided between the first and second end portions 50, 52 to facilitate connection.

As illustrated, the second connector portion 46 is mounted to the first end portion 50. As a result, the second connector portion 46 is able to removably couple with the first connector portion 44 on the flow generator 14 when the adapter 48 is coupled to the outlet 24. In the illustrated embodiment, the first connector portion 44 is in the form of a first conductor and the second connector portion 46 is in the form of a second conductor. Also, the second conductor 46 is bridged with an identifying element, in the form of a resistor, that provides the identifying feature unique to a specific peripheral component.

In use, the adapter 48 is attached to the outlet 24 so that the second conductor 46 is electrically coupled to the first conductor 44. In the illustrated embodiment, the second conductor includes a metallic pin 56 with an axially extending opening 58 and the first conductor includes a metallic pin 60. The axially extending opening 58 of the metallic pin 56 receives the metallic pin 60 therein to electrically couple the first and second conductors 44, 46. However, the first and second conductors 44, 46 may be electrically coupled in any other suitable manner. Once coupled, the controller 40 can detect the resistance provided by the resistor bridged with the second conductor 46. The resistance is unique to a particular peripheral component so the controller 40 can recognize the specific peripheral component by the resistance. Once recognized, the appropriate operating parameters of the flow generator 14 can be automatically selected by the controller 40 to coordinate with the specified peripheral component.

Figures 9, 10:
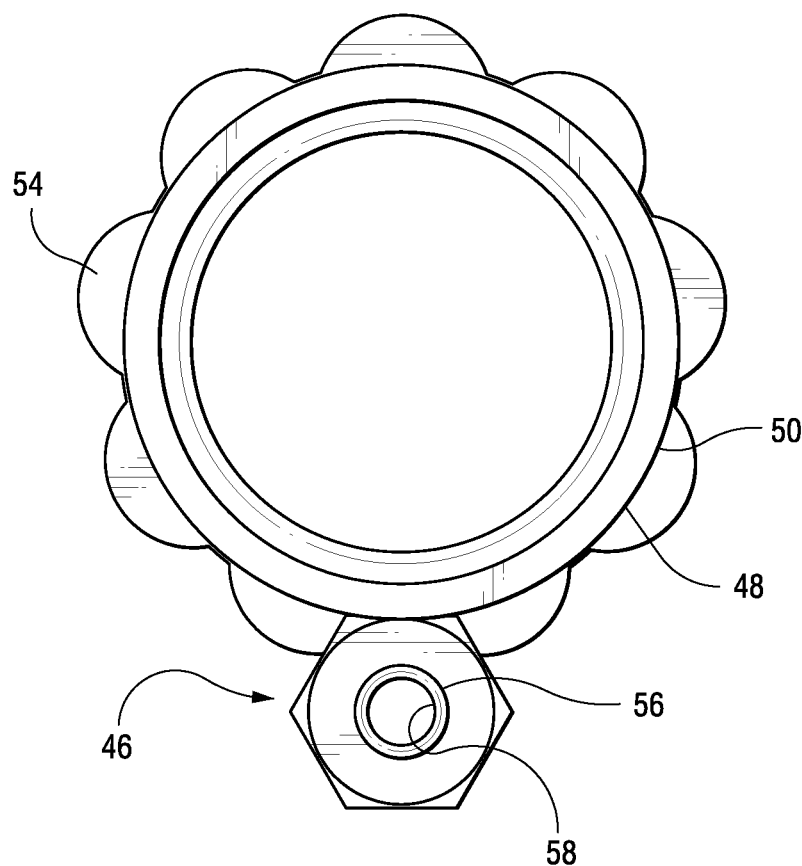
FIG. 9 is a top view of the adapter shown in FIG. 7.
FIG. 10 is a chart illustrating various magnitudes of resistance detected by the recognition system shown in FIG. 2 for embodiments of adapters associated with known masks sold by ResMed Ltd.

For example, FIG. 10 lists three known patient interfaces sold by ResMed Ltd. Each of the patient interfaces is supplied with an adapter 48 having a second connector portion 46 with a unique resistance value. In the illustrated embodiment, the Activa® has a resistor that provides resistance of about 1 ohm, the Mirage® has a resistor that provides resistance of about 2 ohm, and the UltraMirage® has a resistor that provides resistance of about 3 ohm. Accordingly, if the controller 40 detects a 2 ohm resistance when the adapter 48 and second connector portion 46 thereof is engaged with the flow generator 14, the controller 40 will recognize that the Mirage® is coupled to the flow generator 14 and select blower operating parameters that are optimized for the Mirage®.

Thus, the recognition system 10 provides a "plug and play" arrangement wherein the patient can simply couple the adapter 48 and second connector portion thereof 46 to the flow generator 14 to automatically configure the flow generator 10 for a particular peripheral component, e.g., patient interface 18.

It should be understood that more than one peripheral component of the apparatus 12 may be provided with a unique adaptor 48 that automatically configures the flow generator 14 for the associated peripheral component. For example, an adapter 48 may be provided with each of the patient interface 18, air delivery conduit 16, and humidifier (not shown) coupled to the flow generator 14. Each adapter 48 would have a unique identifying feature, as described above, so that the controller 40 can recognize which components are coupled to the flow generator 14. Moreover, the controller 40 can optimize operation of the flow generator 14 to take into account the features of each of the patient interface 18, air delivery conduit 16, humidifier.

In one embodiment, the adapters 48 may be color coded to correspond with particular peripheral components. Moreover, the peripheral component may have a colored element that matches the color of the corresponding adapter 48. This allows the adapters 48 to be easily recognized and associated with the respective component. For example, a patient interface 18 may have a purple colored swivel connector that is accompanied by a purple colored adapter 48. When the purple colored adapter 48 is coupled to the flow generator 14, the controller 40 will optimize the flow generator 14 to correspond with the features of the purple colored patient interface 18. In addition, or in the alternative, the connector and/or peripheral component may have a tactile indicator such as shape, e.g., a polygon, hexagon, etc.

Figure 11:
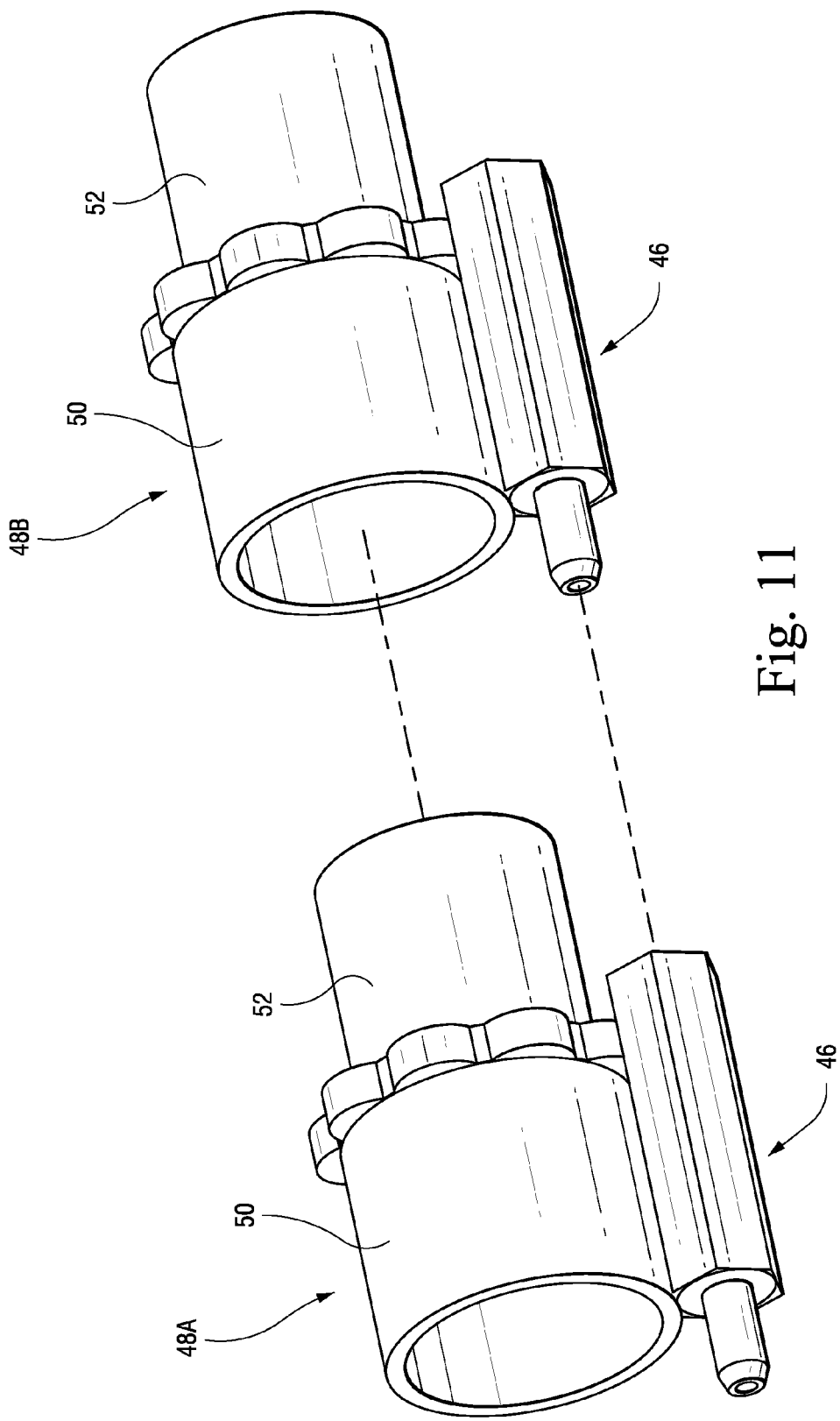
FIG. 11 is a perspective view illustrating stacked adapters of the recognition system.

When multiple peripheral components are coupled to the flow generator 14, e.g., patient interface and humidifier, multiple adapters 48 may be stacked to the outlet 24 of the flow generator 14. For example, a purple adapter 48 associated with a patient interface 18 piggybacked to a yellow adapter 48 associated with a humidifier would signal the controller 40 that both a patient interface 18 and humidifier are attached to the flow generator 14. When piggybacked, one of the adapters 48A is coupled to the flow generator 14 as discussed above and the second adapter 48B is coupled to the first adapter 48A such that the first end portion 50 of the second adapter 48B is attachable to the second end portion 52 of the first adapter 48A and the second end portion 52 of the second adapter 48B is attachable to the air delivery conduit 16 as shown in FIG. 11. Moreover, the conductor 46 of the second adapter 48B is electrically coupled to a rear portion of the conductor 46 of the first adapter 48A. In one embodiment, the adapter 48B may be structured such that it cannot receive a plug from a downstream connector, rather it can only plug into the adapter 48A closer to the flow generator, so as to impose a limitation on the order of attachment. However, it is preferred that the adapters can be attached in random order, to facilitate the connector assembly operation.

The piggyback value of two resistor values wired in parallel could be recognized via simple electronics (e.g., 1/R Total=$1/R_1 + 1/R_2$, where $R_1$ is the resistor value associated with the patient interface and $R_2$ is the resistor value associated with the humidifier). The value of (1/R Total) would relate to a blower setting that adjusts the operating parameters to function optimally with the specific features of both the selected patient interface and humidifier. This arrangement eliminates user intervention to match peripheral components for optimal performance of the connected system.

Figure 12:
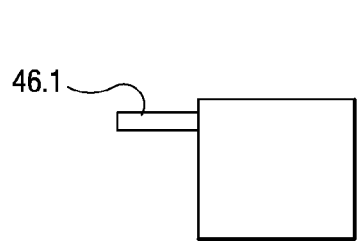
FIGS. 12 and 13 illustrate schematic side views of adapters/connectors according to further embodiments of the present invention.
Figure 13:
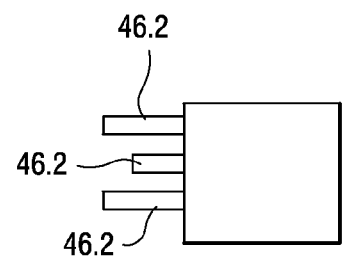

It should be understood that the recognition system 10 may have any suitable structure to enable the controller 40 to automatically recognize selected peripheral components. In the illustrated embodiment, an adapter 48 incorporating an identifiable resistor is utilized to identify the peripheral component. However, the identifying element may have any suitable identifiable structure, e.g., impedance (e.g., using holes of various sizes), microswitches, infrared detectors, variable length pins, variable number of pins, variable pin mountings, spring loads, etc. For example, one embodiment may incorporate one or more variable length pins 46.1 on the end of the connector that can either incorporate a microswitch (or series of switches depending on length) or operate a variable resistor whose value is determined by the length of the pin, e.g., how far the pin pushes a lever operating variable resistor. A series of microswitches, e.g., 6 switches, located around the connector could be operated by pins 46.2 to either the on or off position, similar to a remote control. See, e.g., FIGS. 12 and 13.

Alternatively, the adaptor and/or a component thereof such as a pin may include a coded portion that encodes the flow generator with the peripheral component. This is similar to how a camera film housing encodes the camera with the camera film, upon loading of the housing into the camera.

In another embodiment, the second connector portion 46 may be provided as a separate key, separate from the adapter 48, that is engagable with the first connector portion 44 provided on the flow generator 14. Thus, the adapter 48 may be eliminated and the air delivery conduit 16 may connect directly to the outlet 24 of the flow generator 14.

Also, the controller 40 may identify the peripheral component in any suitable manner. That is, an identifying feature associated with the peripheral component may be communicated to the controller 40 in any suitable manner. For example, the identifying feature may be incorporated into the peripheral component, e.g., patient interface, itself and be communicated to the controller 40 via a wire extending from the peripheral component to the flow generator 14. Alternatively, the identifying feature may be communicated to the controller 40 wirelessly, e.g., RFID, IR, prismatic, smart card (computer chip). In "wireless" embodiments, the controller 40 would be coupled to a receiver adapted to receive signals transmitted by the identifying component associated with the peripheral component.

In another embodiment, the peripheral component may include a bar code with identifying information so that the peripheral component may be moved past a bar code reader provided on the flow generator 14 that will allow the controller 40 to identify the specific peripheral component being utilized.

Also, other information may be provided by the identifying component, e.g., a log of the patient's use, components used during each use, end of life service indication, etc.

The flow generator 14 may include one or more indicator lights to indicate that the peripheral components have been recognized and/or identified. For example, as shown in FIGS. 2 and 3, the flow generator 14 includes a red light 62 that indicates that the component has not yet been recognized (FIG. 2), and a green light 64 that indicates that the adapter 48 is connected and the associated component has been recognized. Thus, the indicator lights may provide positive feedback regarding connection and blower set-up status. The different lights may also indicate different peripherals and confirm correct alignment, e.g., one light for an Activa® mask, another light for an UltraMirage® Full Face Mask, etc.

In the illustrated embodiment, the adapter 48 must be properly aligned with the outlet 24 and the first connector portion 44 to enable the second connector portion 46 to couple with the first connector portion 44. However, the first and second connector portions 44, 46 may be configured and arranged so orientation of the adapter 48 with respect to the outlet 24 does not matter. Moreover, the flow generator will continue to operate even if one or more components of the recognition system are not employed, although the operating characteristics may not be optimized for the particular component in use.

The recognition system 10 is advantageous in that it allows the flow generator 14 to be optimized to function with the connected peripheral components. This minimizes patient intervention to setup the flow generator 14, and therefore improves ease of use.

Leak Testing on Manufacturer Line

Figure 14:
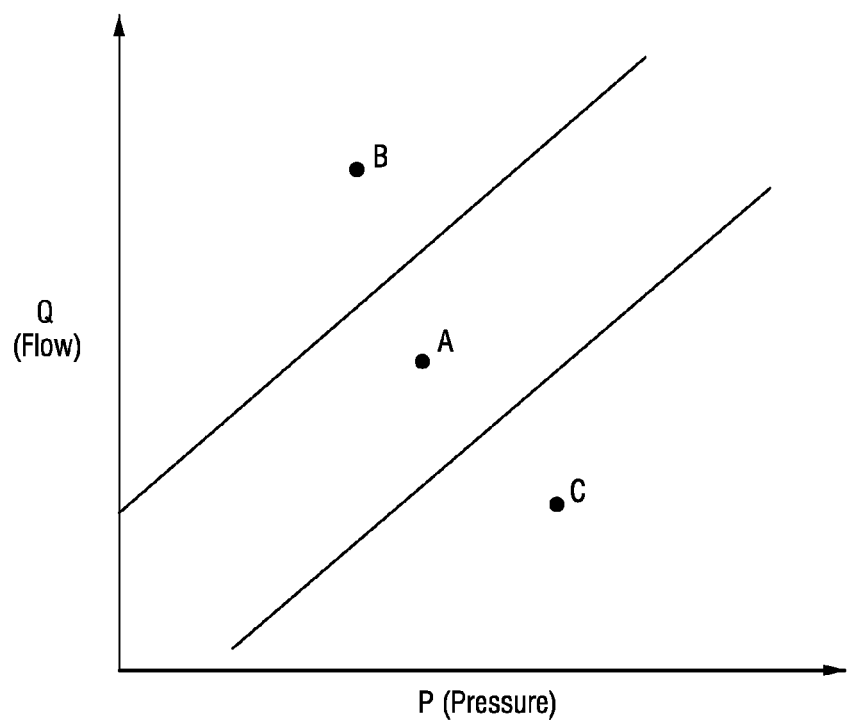
FIG. 14 is a graph illustrating upper and lower ranges preferred by manufacturers of patient interfaces for flow vs. pressure.
Figure 15:
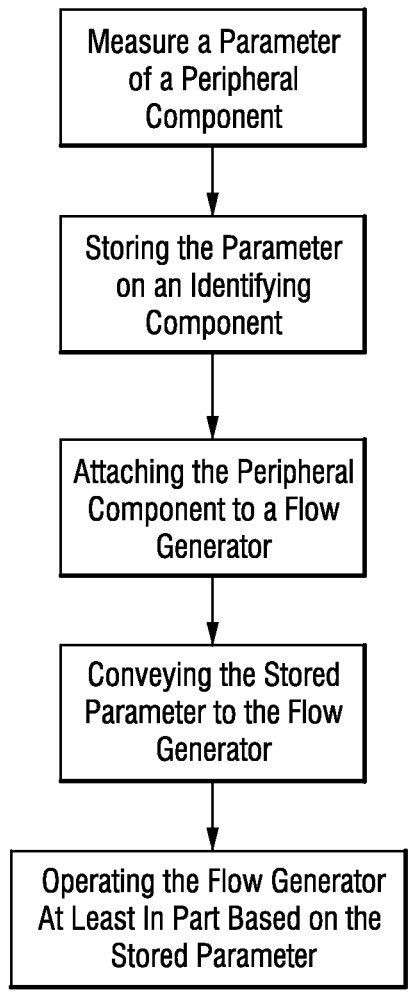
FIG. 15 is a flow chart illustrated an embodiment of a method for operating a flow generator.

Typically, manufacturers test manufactured patient interfaces on the manufacturing line for leak and require that they fall within upper and lower ranges in flow vs. pressure curve to ensure that each patient interface can be used with a flow generator. The flow vs. pressure curve measures for intended, e.g., vents, and unintended sources of leak. Thus, a patient interface falling at A in FIG. 14 would be acceptable, and patient interfaces falling at B and C in FIG. 14 would not be acceptable. If a recognition system 10 is utilized, the leak testing results of the patient interface may be provided on an identifying component, e.g., smart card, and transferred to the controller 40 in use. FIG. 15 is a flow chart illustrating an exemplary method for operating a flow generator. With this information, the controller 40 can optimize the flow generator 14 to compensate for the measured operating parameter of the patient interface. That is, the specific parameters of the patient interface are compensated at the flow generator 14. This allows the typical range requirements to be eliminated so that masks falling at B and C in FIG. 14 can be utilized. Thus, manufacturing design constraints may be reduced, so that patient interfaces may be used that would not typically be used due to manufacturing standards.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A component of a continuous positive airway pressure (CPAP) system, the CPAP system including a flow generator that is adapted to generate a supply of pressurized breathable gas that is provided from an outlet of the flow generator to a patient via an airflow path, the component comprising:
   a body that is configured to be physically attachable to or adjacent the outlet of the flow generator and included in the airflow path that communicates, at least in part, the supply of pressurized breathable gas to the patient; and
   an identifying element that is included with the body and providing an identifying feature that is associated with a peripheral component that is configured to operate in the CPAP system, the identifying element set to communicate with the flow generator to provide the supply of pressurized gas to the patient via the airflow path,
   wherein the identifying feature provided from the identifying element is set to be communicated to the flow generator so that at least one appropriate operating parameter of the flow generator may be processed by the flow generator and the supply of pressurized breathable gas set in accordance with the processing,
   wherein the identifying feature includes at least one of the following: a log of patient use, an end of life service indication, components used during each use, and/or a leak parameter that indicates a measured leak value associated with the peripheral component,
   wherein the body is a separate structural body from the peripheral component that is associated with the identifying feature.

2. The component of claim 1, wherein the body is an adapter that is adapted to interface with the flow generator.

3. The component of claim 1, wherein the identifying feature is set to be communicated, at least in part, wirelessly to the flow generator.

4. The component of a continuous positive airway pressure (CPAP) system of claim 1, wherein the identifying feature includes the log of patient use.

5. The component of a continuous positive airway pressure (CPAP) system of claim 1, wherein the identifying feature includes the end of life service indication.

6. The component of a continuous positive airway pressure (CPAP) system of claim 1, wherein the identifying feature includes the components used during each use.

7. The component of a continuous positive airway pressure (CPAP) system of claim 1, wherein the identifying feature includes the leak parameter that indicates the measured leak value associated with the peripheral component.

8. A flow generator of a continuous positive airway pressure (CPAP) system, the flow generator comprising:
   a motor that is configured to generate a supply of pressurized breathable gas that is delivered, via an airflow path, to a patient for treatment, the airflow path configured to include a structural body with an identifying element disposed on or in the structural body, the identifying element including an identifying feature that is related to a peripheral CPAP component that is operable to be a component of the CPAP system;
   an outlet that communicates the generated supply of pressurized breathable gas to the structural body that is physically attachable to the outlet;
   a communication interface that is configured to communicate with the identifying element to retrieve the identifying feature of the identifying element;
   a memory storage medium that is configured to store at least one operating parameter in accordance with the retrieved identifying feature; and
   a controller that is configured to process the stored at least one operating parameter to control the supply of pressurized breathable gas provided to the patient for treatment,
   wherein the identifying feature includes at least one of the following: a log of patient use, an end of life service indication, components used during each use, and/or a leak parameter that indicates a measured leak value associated with the peripheral component,
   wherein the structural body is a separately provided from the peripheral CPAP component.

9. The flow generator of claim 8, wherein the structural body is an adapter.

10. The flow generator of claim 8, wherein the identifying feature includes an airflow related parameter of the peripheral CPAP component.

11. The flow generator of claim 10, wherein the controller is further configured to adjust how the supply of pressurized breathable gas is provided to the patient for treatment based on the airflow related parameter.

12. The flow generator of claim 10, wherein the peripheral CPAP component is a patient interface.

13. A component of a continuous positive airway pressure (CPAP) system, the CPAP system including a flow generator adapted to generate a supply of pressurized breathable gas provided from an outlet of the flow generator to a patient via an airflow path, the component comprising:
   an adapter body configured to be included in the airflow path that communicates, at least in part, the supply of pressurized breathable gas from an outlet of the flow generator to the patient; and
   an identifying element included with the adapter body and having an identifying feature associated with a separately provided peripheral component configured to operate in the CPAP system, the identifying element set to communicate with the flow generator, the peripheral component being a structurally separate body from the adapter body, wherein the identifying feature provided from the identifying element is set to be communicated to the flow generator so that at least one appropriate operating parameter of the flow generator may be processed by the flow generator and the supply of pressurized breathable gas set in accordance with the processing, wherein the identifying feature includes at least one of the following: a log of patient use, an end of life service indication, components used during each use, and/or a leak parameter that indicates a measured leak value associated with the peripheral component.

14. The component of claim 13, wherein the identifying feature is set to be communicated, at least in part, wirelessly to the flow generator.

15. The component of claim 13, wherein the identifying element is a resistor and the identifying feature is a particular resistance.

16. The component of claim 13, wherein the identifying feature includes the log of patient use.

17. The component of claim 13, wherein the identifying feature includes the end of life service indication.

18. The component of claim 13, wherein the identifying feature includes the components used during each use.

19. The component of claim 13, wherein the identifying feature includes the leak parameter that indicates the measured leak value associated with the peripheral component.

\* \* \* \* \*